United States Patent
Martter et al.

(10) Patent No.: US 6,289,176 B1
(45) Date of Patent: Sep. 11, 2001

(54) ELECTRICALLY HEATED AIR FRESHENERS

(75) Inventors: Robert H. Martter; Craig C. Sundberg, both of Erie, PA (US)

(73) Assignee: The Erie Ceramic Arts Company, Erie, PA (US)

( * ) Notice: Subject to any disclaimer, the term of this patent is extended or adjusted under 35 U.S.C. 154(b) by 0 days.

(21) Appl. No.: 09/650,823

(22) Filed: Aug. 30, 2000

Related U.S. Application Data

(62) Division of application No. 08/254,181, filed on Jun. 6, 1994, now Pat. No. 6,141,496.

(51) Int. Cl.[7] ............................................. A61M 16/00
(52) U.S. Cl. ...................................... 392/392; 392/390
(58) Field of Search ............................ 392/390, 392, 392/403, 404; 219/543; 338/307, 308, 309

(56) References Cited

U.S. PATENT DOCUMENTS

| | | | |
|---|---|---|---|
| 2,882,187 | * 4/1959 | Kwate | 428/427 |
| 3,396,055 | * 8/1968 | Hedden et al. | 428/332 |
| 3,990,848 | 11/1976 | Corris | 21/126 |
| 4,031,353 | * 6/1977 | Reuda Segura | 392/438 |
| 4,145,001 | 3/1979 | Weyenberg et al. | 239/56 |
| 4,383,377 | 5/1983 | Crafton | 34/60 |
| 4,571,485 | 2/1986 | Spector | 219/276 |
| 4,725,712 | * 2/1988 | Schroeder | 392/392 |
| 4,849,606 | 7/1989 | Martens, III et al. | 219/271 |
| 5,657,532 | * 8/1997 | Alexander et al. | 219/543 |
| 6,044,202 | * 3/2000 | Junkel | 392/390 |
| 6,141,496 | 10/2000 | Sunberg et al. | 392/390 |

* cited by examiner

*Primary Examiner*—Sang Paik
(74) *Attorney, Agent, or Firm*—Rankin, Hill, Porter & Clark LLP

(57) ABSTRACT

The present invention provides an electrically heated air freshener for producing a scent comprising a housing having a receptacle for supporting a fragrance block, the fragrance block comprising a material that volatilizes upon heating and a porcelain enamel metal substrate comprising a metal substrate having a porcelain enamel coating bonded thereto. The porcelain enamel coating has bonded thereto a resistance strip for generating heat upon application of an electrical current and a conductive strip for conducting electrical current to the resistance strip.

11 Claims, 3 Drawing Sheets

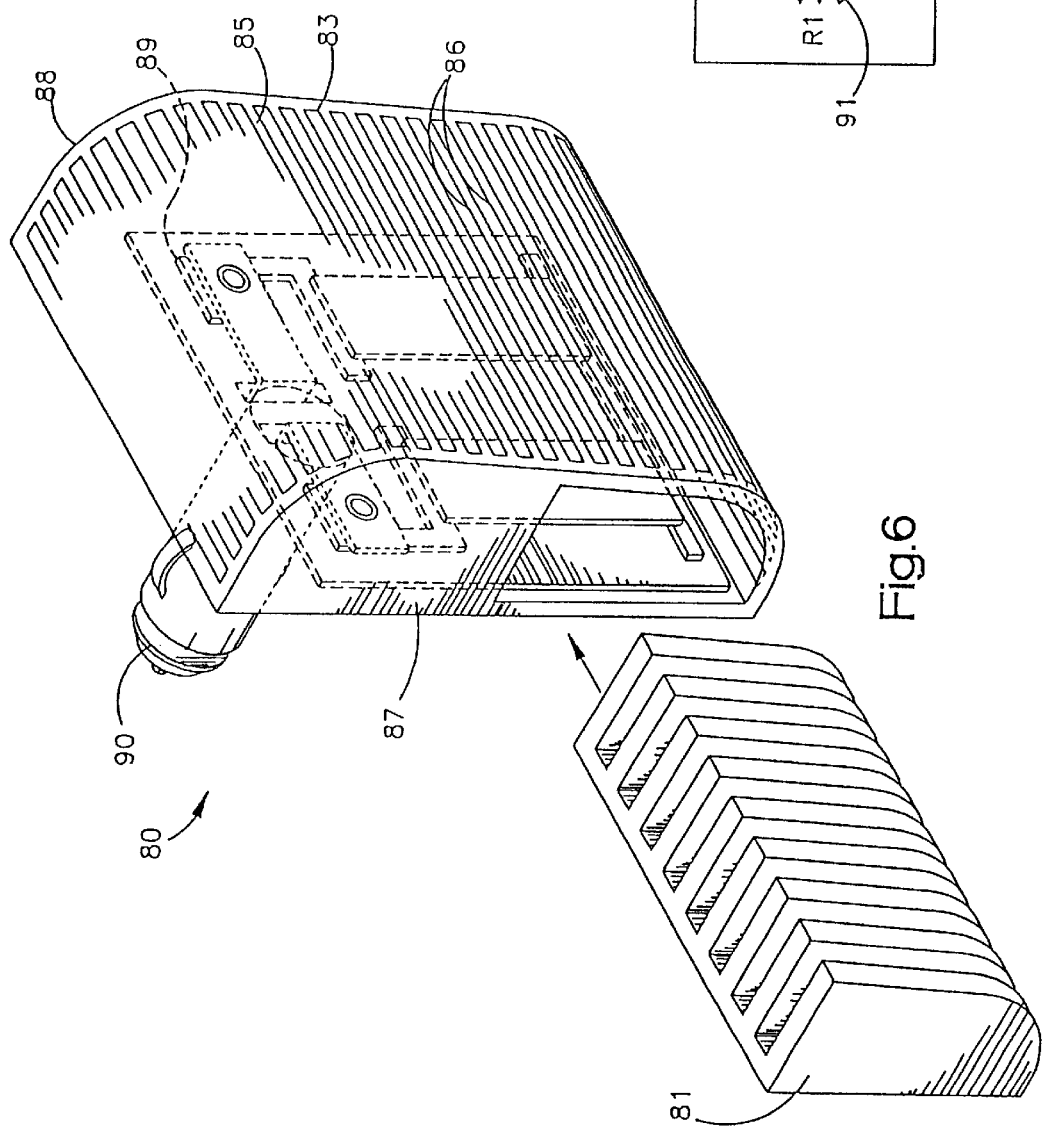

ELECTRICALLY HEATED AIR FRESHENERS

RELATED APPLICATIONS

This application is a divisional application of patent application Ser. No. 08/254,181 filed Jun. 6, 1994 Now U.S. Pat. No. 6,141,496 entitled ELECTRICALLY HEATED AIR FRESHENERS.

FIELD OF THE INVENTION

This invention relates to air fresheners having electrical heating devices which vaporize a material to motivate the escape of a scent. More particularly, the invention relates to the use of a structural component in the air freshener comprising a porcelain enameled metal substrate. The substrate serves as a heating device in the air freshener and it comprises a surface layer formed of porcelain enamel and a thick-film, electrically resistive element bonded to the porcelain enamel coating.

BACKGROUND OF THE INVENTION

Electrically heated air fresheners are used for deodorizing and scenting the ambient air in an enclosed space such as in a home or office. These devices utilize a fragrance element that is heated to motivate the escape of a scent into the surrounding atmosphere. This is accomplished by increasing the temperature of the concentrated scenting material to heat scent molecules to a vapor pressure sufficient to escape the concentrated form and dissipate into the ambient air in a relatively high concentration.

Among the prior art devices used for this purpose, is a type using a plastic enclosure with male terminals that can be plugged into a wall outlet. An on/off switch may be provided as well as an LED to indicate the on or off condition. The plastic enclosure may be opened from the top to expose a cavity designed specifically to receive a fragrance block comprising scenting material. The fragrance block is preferably not visible when the top is closed. The floor of the cavity is, for example, a chromed metal plate that is heated by a ceramic body resistor that contacts the underside of the plate. A thermal transfer grease is placed between the ceramic body resistor and the metal heat transfer plate and held into position by a leaf spring. The resistor heats the plate which in turn, heats the fragrance block resting thereon. The plastic enclosure may be provided with adjustable louvers on the top and bottom so that the user may control the rate at which the fragrance is released into the ambient air. Also, the metal plate is preferably provided with side relief or edge openings to allow the air to flow past the plate and around the fragrance block. The above type of prior art device utilizes a conventional phenolic printed circuit board mounted in the fragrance housing separate from the heat transfer plate and the heating device.

Another type of prior art air freshener device is shown in U.S. Pat. No. 4,849,606. In this air freshener device, the fragrance block is supported in a cage-type holder that is sufficiently open so that the block is visible to persons in the vicinity. The heating element in this device is a nichrome wire wound around a fiberglass core. This heating element is positioned within a molded plastic base which in turn is connected to electrical contact prongs or male terminals so that the device may be plugged into a standard wall receptacle. The electrical contact prongs are supported by the molded plastic base.

The prior art air fresheners such as those described above are of somewhat fragile construction and are vulnerable to damage and failure due to the rough treatment that typically may occur during use. Further, the electrical heating portions of such air freshener devices generally comprise multiple pieces or parts.

The air freshener of the present invention reduces the number of parts needed to form the electrical heating portion of the air freshener, facilitates miniaturization, provides an air freshener device that can withstand rough handling and affords other features and advantages heretofore not obtainable.

SUMMARY OF THE INVENTION

The air freshener of the present invention includes a novel means for heating a vaporizable scent material (i.e. fragrance block) to motivate the escape of a scent. The air freshener comprises an enclosure, a heating circuit and a receptacle for holding the fragrance block. The heating circuit comprises a porcelain enamel metal substrate which is a metal substrate having a layer of fused porcelain enamel bonded to the metal substrate. A thick film, electrically resistive heating element is bonded directly to the fused porcelain enamel coating. In the end use assembly the fragrance block is positioned to be heated by the thick film resistive heating element. Suitable electric circuitry is provided to the heating element for supplying the necessary electrical current. The electrical circuitry includes thick film conductors also bonded to the fused porcelain enamel coating. By use of a porcelain enameled substrate one is able to consolidate various functions into a single piece (i.e., electrical control, heating, electrical conduction, etc.). This consolidation can facilitate miniaturization of the air freshener device. The porcelain enameled metal substrate affords another distinct advantage in that it is very durable.

The porcelain enamel metal substrate may also include other circuitry and other mechanical functions such as an on/off switch, a light emitting display (LED) to indicate an on/off condition and integrated terminals to obtain various other functions.

BRIEF DESCRIPTION OF THE DRAWINGS

FIG. 6 shows another embodiment of the invention, wherein the air freshener is adapted for use in connection with an automobile cigarette lighter receptacle; and FIG. 7 is a schematic diagram of the electrical circuit used with respect to the device of FIG. 6.

DESCRIPTION OF THE PREFERRED EMBODIMENT

Figure 1:
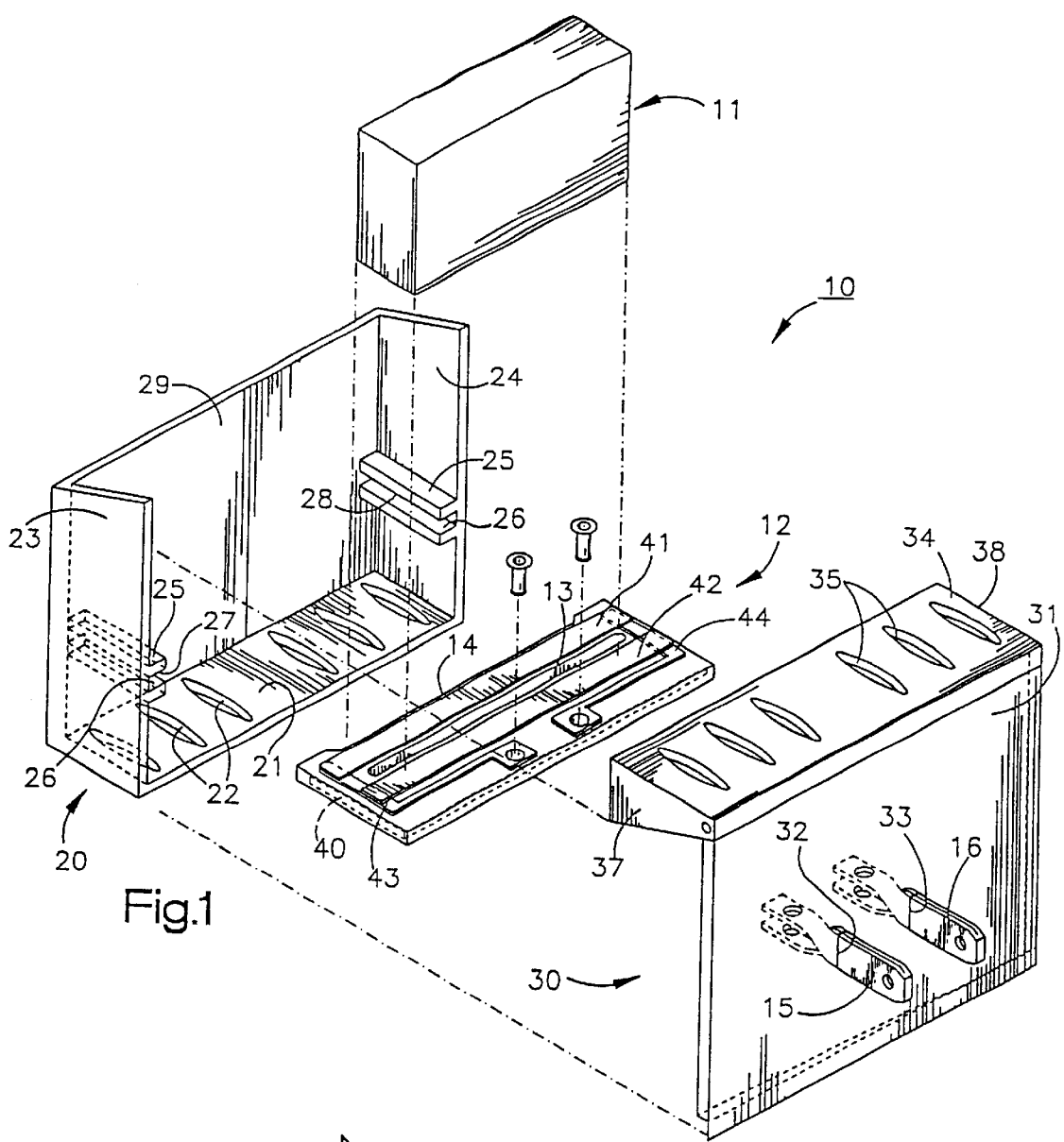
FIG. 1 is an exploded perspective view showing an air freshener embodying the invention.

Referring more particularly to the drawings and initially to FIG. 1, there is shown a fragrance heater or air freshener 10 embodying the invention and adapted to utilize electrical current to heat a fragrance block 11 formed of vaporizable or volatile material to motivate the escape of a scent.

The fragrance heater 10 includes a front section 20 and a rear section 30, which fit together to define an enclosure or housing for the fragrance block 11. The device includes a porcelain enamel metal substrate 12 embodying the invention and provided with a longitudinal slot 13 to aid in the circulation of atmosphere around the fragrance block 11. The one longitudinal side edge of the porcelain enamel metal substrate 12 is also relieved as shown at 14 to provide an additional opening for the circulation of atmosphere. The device is also provided with a pair of electrical male contact prongs 15 and 16 that may be plugged into a standard wall outlet.

The front section 20 includes a floor 21 provided with a plurality of slots or openings 22, and a pair of vertical sidewalls 23 and 24. The interior surface of the sidewalls 23 and 24 are each provided with a pair of parallel horizontal ribs 25 and 26 which define a pair of horizontal slots 27 and 28 respectively, that are dimensioned so as to receive the porcelain enamel metal substrate 12. The front section 20 also has an upright forward wall 29 which may be suitably decorated as desired.

The rear section 30 has an upright back wall 31 with a pair of slots 32 and 33 adapted to receive the electrical contact prongs 15 and 16. The prongs 15 and 16 are securely supported in slots 32 and 33 to facilitate multiple insertions into a wall outlet. The rear section 30 also has a top panel 34 provided with openings or slots 35 to encourage circulation of atmosphere around the fragrance block 11. Although not illustrated, top panel 34 may include a slide panel which allows a user to adjust the size of openings 35. The rear section 30 also has a pair of side portions 37 and 38 at its opposite sides which are adapted to fit together with the tops of the respective sidewalls 23 and 24 of the front section 20.

The porcelain enamel metal substrate 12 incorporates certain novel features provided by the invention. In general, the porcelain enamel metal substrate 12 consists of a porcelain enamel coated metal substrate of the type to be described in more detail below, which comprises a layer of dielectric or porcelain enamel material 39 bonded on to a metal substrate or base 40. In accordance with the invention, at least one thick film resistor strip is bonded to the surface of the porcelain enamel coating. Upon passage of electrical current through the resistor strip the strip generates heat for volatilizing the fragrance block. In the embodiment shown, a pair of longitudinally extending thick film resistor strips 41 and 42 are bonded to the porcelain enamel coating and provided on the top face of the porcelain enamel metal substrate 12. Also, a pair of thick film conductors 43 and 44 are positioned in contact with the opposite ends of the resistors 41 and 42, and they include terminal portions adapted to make contact with the electrical contact prongs 15 and 16 preferably via mechanical rivets as shown in FIGS. 1 and 2.

Figure 2:
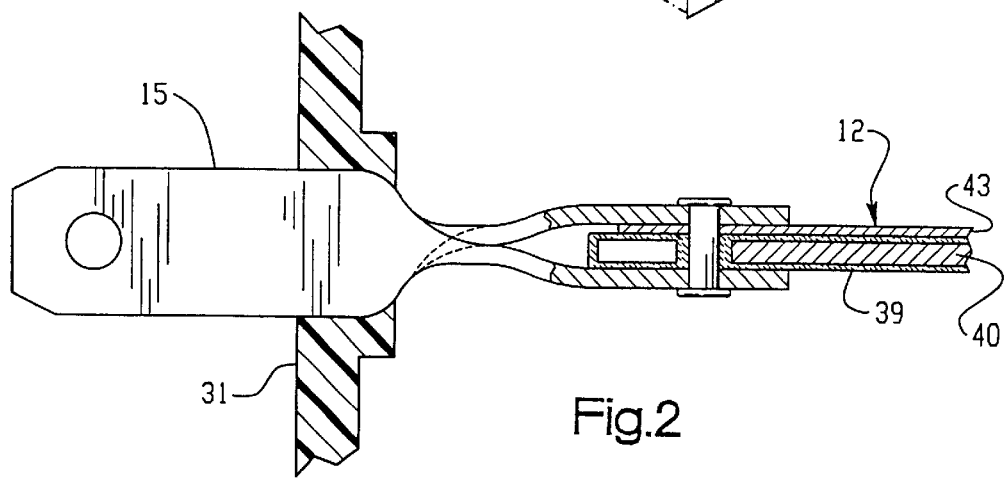
FIG. 2 is a broken-away, cross-sectional view of one of the male electrical contact prongs and a portion of the porcelain enamel metal substrate of FIG. 1.

FIG. 2 further illustrates the electrical contact prong 15 having a forked end and a mechanical rivet adapted to securely engage the porcelain enamel metal substrate and electrically contact thick film conductor 43. It will be appreciated that instead of forking the end of contacts 15 and 16 it may be possible to utilize a single flat end and a mechanical rivet to engage conductor 43. It will also be appreciated that any number of conventional methods may be used in the present invention for accessing a porcelain enamel metal substrate by electrical contact prongs that are received in a common household 120VAC outlet. Such conventional methods include, for example, soldering, screws, bolts and nuts, etc. Further, it will be appreciated that various types of electrical contact prongs may be utilized such that the air freshener may be used in other conventional wall outlets such as a 240VAC outlet.

It will be noted that the thick film resistor strips 41 and 42 and the thick film conductors 43 and 44 may be applied to the bottom surface of the porcelain enameled metal substrate 12 if desired. If applied to the top surface, they will be in intimate contact with the fragrance block 11. However, if applied to the bottom surface, the heat generated will be transmitted through the substrate to the top surface thereof where the substrate will be in intimate contact with the fragrance block 11. In the embodiment of FIG. 1, if the air freshener is intended for us whereby the user will be changing fragrance block 11, it is preferred to orientate the circuitry on the bottom of substrate 11 so as to minimize the possibility of a user touching such circuitry and obtaining an electrical shock.

It will be appreciated that in applications wherein the porcelain enamel metal substrate is located adjacent a housing sidewall having openings formed therein, the side of the substrate which has no circuitry may be artistically decorated to create an aesthetically pleasing sight when such side of the substrate is viewed by a user through the openings in the sidewall of the housing.

The thick film resistor strip or strips employed in the present invention will typically produce about 1.5 watts of heating power at 110 to 120VAC. The resistance for such a heater at 120VAC will be about 9600 ohms. The exact target and tolerance will be determined by the circumstances such as the size of the fragrance block, the material used to form the block, the desired rate of volatilizing the block, etc.

The thick film resistor strips 41 and 42 as well as the thick film conductor elements 43 and 44, may be formed using conventional resistive and conductive thick films. An example of a preferred resistive thick film is a product sold by Electro Science Labs under the trade designation 3113 TF Resistor. An example of a preferred conductive thick film is a product sold by the Ferro Corporation of Cleveland, Ohio, under the trade designation FX-86-010.

One typical procedure for forming the porcelain enameled metal substrate 12 is accomplished as follows:

A decarburized steel base is formed by stamping a coupon from a steel sheet of a desired thickness. The coupon is treated by pickling or some other conventional metal pretreatment process. The resulting product is emersed in a conventional acidic copper sulphate solution for a brief period of time (about 1 minute) after which it is dipped in a slurry of dielectric particles such as conventional porcelain enamel particles.

Within the slurry are fixed cathodes and the preliminary assembly or substrate is connected in such a way that it acts as an anode and attracts the solid particles in the slurry by electrophoresis. As a result, the dielectric particles are deposited on both surfaces of the base or substrate 40 to form a coating.

When the coated product is removed from the slurry, it is dried and then heated or fired to a sintering temperature such as around 1500° F. Of course, it will be appreciated that the exact sintering or fusing temperature and time will depend upon the particular dielectric material being used.

Any number of conventional dielectric coating materials may be used in connection with the present invention. Such coatings may be classified as either "porcelain enamel", "glass" or "ceramic". Such "porcelain enamel" or "glass"

coatings may be referred to as "vitreous" coatings. Such "ceramic" coatings may be referred to as "devitrified" coatings. Examples of such coatings may be found in Lim et al., U.S. Pat. No. 5,002,903; Ohmura et al., U.S. Pat. No. 4,361,654; Kaup et al., U.S. Pat. No. 3,935,088; Moritsu et al., U.S. Pat. No. 4,172,733; Van derVliet, U.S. Pat. No. 4,085,021; Hang et al., U.S. Pat. No. 4,256,796; Andrus et al., U.S. Pat. No. 4,358,541; Chyung, U.S. Pat. No. 4,385,127; Gazo et al. U.S. Pat. No. 3,841,986 and Hughes U.S. Pat. No. 3,575,838. Applicants hereby incorporate by reference the coatings disclosed in such U.S. Patents including the methods of making such coatings and applying such coatings to a metal substrate. As used herein the term "porcelain enamel" is intended to encompass all of the aforementioned coatings.

It will be appreciated that any number of coating techniques and baths, dielectric or resistive coatings, and firing techniques may be used all in accordance with the invention. Further, it will be appreciated that any number of base metal substrates may be employed in the present invention other than steel, such as, for example, aluminum, copper and stainless steel.

Conventional resistive and conductive thick films may be applied to the porcelain enamel coating 39 by spraying, silk screening, brushing, dipping or by other conventional application techniques. A preferred method of producing conductive or resistive paths such as paths 43, 44 and 41, 42 is to screen print the thick film in the desired configuration upon the porcelain enamel coating 39 and then firing the coated substrate at about 625° C. for about five minutes at peak temperature.

Figure 3:
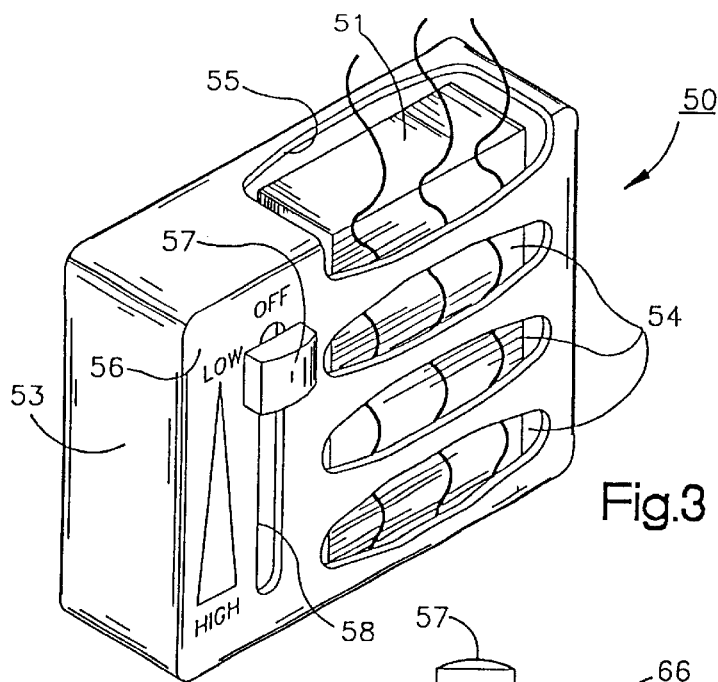
FIG. 3 shows a perspective view of an alternate form of the invention, wherein the air freshener device is provided with an integral on/off switch and a rheostat.
Figure 4:
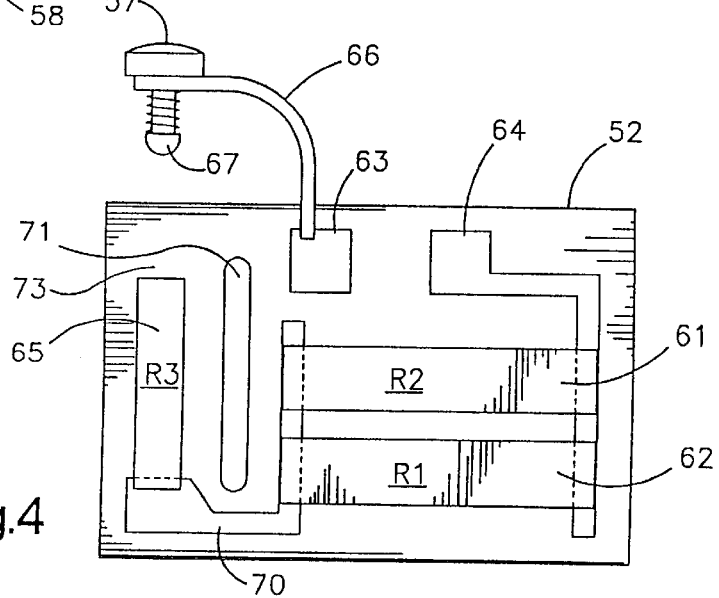
FIG. 4 is a front view of the porcelain enamel metal substrate and control button of FIG. 3.

FIGS. 3 illustrates an alternate form of the invention, wherein a variable rheostat is provided so that the user can control the rate of heating of the fragrance block. The air freshener 50 has suitable sidewalls, front and back walls, and top and bottom panels to define an enclosure adapted to receive a fragrance block 51. Also, the air freshener 50 has means to support a vertically disposed porcelain enamel metal substrate 52 similar in some respects to the porcelain enamel metal substrate 12 of the embodiment of FIG. 1. The porcelain enamel metal substrate 52 is supported within the enclosure along the back wall as indicated generally at 53.

The housing has a plurality of slots 54 formed in the front panel and a larger opening or top opening 55 formed in the top panel. The fragrance block 51 is inserted through the opening 55 so that it rests on the bottom panel.

The front panel has a right hand portion in which the slots 54 are formed and left hand or control panel portion 56 with a slidable control button 57 adapted to be moved by the user to control the rate of heating. The control button 57 slides in a vertical slot 58. Through the use of a variable resistor as described below, control button 57 provides a full "OFF" position, and a variety of positions from "LOW" to a full on or "HIGH."

The porcelain enamel metal substrate 52 includes a pair of thick film resistor strips 61 and 62 to provide the means for heating the fragrance block 51. Also, bonded to the porcelain enamel metal substrate 52 are thick film conductive strips 63, 64 and 70. The resistor and conductor strips may be applied in the same manner described with respect to the embodiment of FIG. 1. The conductor strips 63 and 64 have terminal portions to provide contact with the electrical contact prongs via mechanical rivets along the line as shown in the embodiment of FIG. 1.

A thick film variable or control resistor strip 65 is bonded to the porcelain enamel metal substrate 52 adjacent the thermal barrier slot 71 and parallel thereto. Barrier slot 71 serves to inhibit the transfer of heat from variable resistor strip 65 to the heater area containing resistor heater strips 61 and 62. The variable resistor strip 65 is in contact at its lower end with the conductor strip 70 which in turn contacts the respective ends of the resistor strips 61 and 62. The conductor strip 64 contacts the opposite ends of the resistor strips 61 and 62. The control button 57 has an electrical contact element 67 adapted to engage the control resistor strip 65 as the control button 57 is moved vertically in the slot 58. Also, the control button 57 is electrically connected by a flexible lead (wire) 66 to the thick film conductive section 63, which section 63 in turn contacts the respective electrical contact prong. When control button 57 is moved all the way up in slot 58, contact element 67 is located above resistor strip 65 in an "off" position indicated generally at 73.

Figure 5:
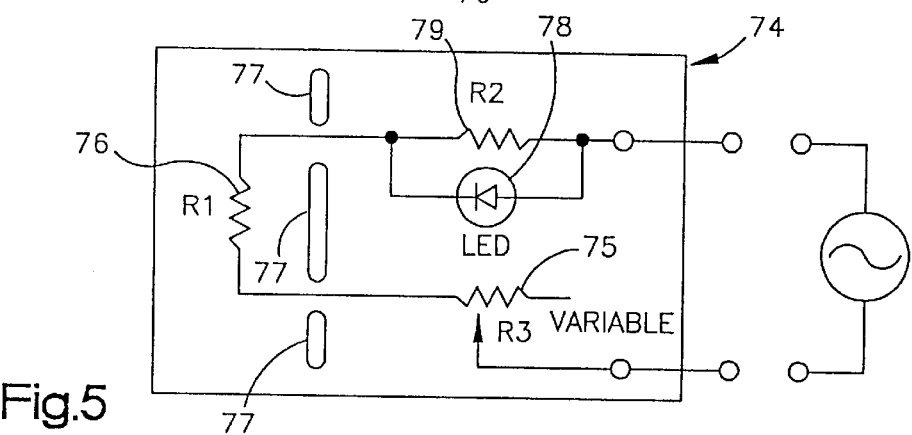
FIG. 5 is a schematic diagram illustrating the electrical circuit utilized in another embodiment made in accordance with the present invention.

Referring to FIG. 5 there is shown a schematic diagram of an alternative electrical circuit that may be used in the present invention. The porcelain enamel metal substrate which is generally indicated at 74 includes a variable resistor generally indicated at 75, a heating resistance indicated at 76, thermal barrier slots indicated at 77 and a light emitting display (LED) generally indicated at 78. Included in parallel with LED 78, or across LED 78 is thick film resistor 79. The LED 78 indicates whether or not the circuit is energized and the LED 78 will dim as voltage is reduced to the heating resistance 76.

FIGS. 6 and 7 show an alternate form of the invention, wherein an air freshener or fragrance heater device 80 is adapted to be plugged into a conventional cigarette lighter receptacle of an automobile. The device has a housing 83 for receiving a special fragrance block 81 which is adapted to be inserted through an opening in the sidewall 87. Sidewall 88 is located opposite sidewall 87. The housing 83 has a curved front wall 85 with a plurality of lateral slots 86 to encourage circulation of atmosphere.

Located within the housing 83 is a vertically positioned porcelain enamel metal substrate 89 with multiple thick film resistance strips that afford a resistance 91 and multiple conductor 92 strips bonded thereto for heating the fragrance block 81. The housing 83 is also provided with a standard connector plug 90 which is adapted to be inserted into the vehicle cigarette lighter receptacle. The connector 90 is electrically connected to the resistance 91 through the thick film conductor strips bonded to the porcelain coating of the porcelain enamel metal substrate 89. In the case of an automobile-type air freshener as shown in FIGS. 6 and 7, wherein 12 volts DC will be used, the resistance 91 will typically be about 96 ohms.

As an alternate form of the device shown in FIGS. 6 and 7, the housing 83 may in turn be provided with a receptacle for a cigarette lighter so as to enable the user to use not only the fragrance block 81, but the lighter receptacle as well.

It will be also understood that the particular porcelain enamel metal substrate may have its circuit components on the side facing the fragrance block or vice verse. Also, in some instances, the porcelain enamel metal substrate may be molded into a solid plastic body forming the housing for the fragrance holder.

While the invention has been shown and described with respect to specific embodiments thereof, this is intended for the purpose of illustration rather than limitation and other variations and modifications of the specific devices herein shown and described will be apparent to those skilled in the art all within the spirit and scope of the present invention.

Accordingly, the patent is not to be limited in scope and effect to the specific embodiments herein shown and described nor in any other way that is inconsistent with the extent to which the progress in the art has been advanced by the invention.

What is claimed is:

1. An electrically heated air freshener for producing a scent comprising:
   A. a housing having a receptacle for supporting a fragrance block, said fragrance block comprising a material that volatilizes upon heating; and
   B. a porcelain enamel metal substrate comprising a metal substrate having a porcelain enamel coating bonded thereto, said porcelain enamel coating having bonded thereto:
      i. a resistance strip for generating heat upon application of an electrical current; and
      ii. a conductive strip for conducting electrical current to said resistance strip;
   wherein said porcelain enamel metal substrate includes a variable resistance strip bonded to said porcelain enamel coating.

2. An air freshener as set forth in claim 1 wherein said housing includes a movable control button for contacting said variable resistance strip at various locations thereby facilitating the supply of varying amounts of electrical current to said resistance strip.

3. An air freshener as set forth in claim 1 wherein said porcelain enamel metal substrate is located immediately proximate to and in contact with said fragrance block.

4. An air freshener as set forth in claim 1 wherein said resistance strip comprises a fired thick film resistance material.

5. An air freshener as set forth in claim 1 wherein said conductor strip comprises a fired thick film conductor material.

6. An air freshener as set forth in claim 1 wherein said porcelain enamel metal substrate includes two or more of said resistance paths.

7. An air freshener as set forth in claim 1 wherein said porcelain enamel metal substrate includes a thermal barrier slot for inhibiting the transfer of heat along said porcelain enamel metal substrate.

8. An air freshener as set forth in claim 1 wherein said housing includes a plurality of slotted openings to facilitate the flow of air around said fragrance block.

9. An air freshener as set forth in claim 1 wherein said porcelain enamel metal substrate includes a base substrate comprising steel.

10. An air freshener as set forth in claim 1 wherein said housing includes a protruding electrical connector adapted for insertion into the cigarette lighter receptacle of a vehicle, said electrical connector being electrically connected to said conductive strip of said porcelain enamel metal substrate.

11. An air freshener as set forth in claim 1 wherein said porcelain enamel metal substrate includes a light emitting display.

* * * * *